United States Patent
Vadali et al.

(10) Patent No.: US 9,975,864 B2
(45) Date of Patent: May 22, 2018

(54) PREPARATION OF COBICISTAT INTERMEDIATES

(71) Applicant: Mylan Laboratories Ltd., Hyderabad (IN)

(72) Inventors: Lakshmana Rao Vadali, Hyderabad (IN); Rameshbabu Konda, Hyderabad (IN); Ramesh Dandala, Hyderabad (IN)

(73) Assignee: Mylan Laboratories Limited (IN)

( * ) Notice: Subject to any disclaimer, the term of this patent is extended or adjusted under 35 U.S.C. 154(b) by 0 days. days.

(21) Appl. No.: 15/100,361

(22) PCT Filed: Dec. 2, 2014

(86) PCT No.: PCT/IB2014/066500
§ 371 (c)(1),
(2) Date: May 31, 2016

(87) PCT Pub. No.: WO2015/083066
PCT Pub. Date: Jun. 11, 2015

(65) Prior Publication Data
US 2016/0297780 A1 Oct. 13, 2016

(30) Foreign Application Priority Data
Dec. 3, 2013 (IN) .......................... 5570/CHE/2013

(51) Int. Cl.
C07D 295/26 (2006.01)
C07D 203/24 (2006.01)
C07D 417/12 (2006.01)

(52) U.S. Cl.
CPC ......... *C07D 295/26* (2013.01); *C07D 203/24* (2013.01); *C07D 417/12* (2013.01); *C07B 2200/13* (2013.01)

(58) Field of Classification Search
CPC .. C07D 211/00; C07D 211/06; C07D 295/26; C07D 203/24
USPC ........................................................ 546/186
See application file for complete search history.

(56) References Cited

U.S. PATENT DOCUMENTS

| 8,148,374 B2 | 4/2012 | Desai et al. |
| 8,497,396 B2 | 7/2013 | Polnlaszek et al. |
| 9,115,100 B2 | 8/2015 | Polniaszek |
| 9,346,796 B2 | 5/2016 | Cullen |

FOREIGN PATENT DOCUMENTS

| WO | 2012/045007 | 4/2012 |
| WO | 2013/116715 | 8/2013 |
| WO | 2014/057498 | 4/2014 |

OTHER PUBLICATIONS

Written Opinion and Search Report relating to corresponding International Application No. PCT/IB2014/066500 dated Feb. 17, 2015.
Bavin, M. ,"Polymorphism in Process Development", Chemistry & Industry, Society of Chemical Industry, London, GB, vol. 21, Aug. 21, 1959, pp. 527-529.
Anderson et al., "Tools for Purifying the Product: Column Chromatography, Crystallization and Reslurring", Practical Process Research and Development, Academic Press, San Diego, Jan. 1, 2000, pp. 223-247.
David M Hodgson, Dimerization and Isomerization Reactions of alpha-Lithiated Terminal Aziridines, J. Org. Chem., vol. 72, No. 26, 2007.

*Primary Examiner* — Rita J Desai

(57) ABSTRACT

The present disclosure provides crystalline piperidine sulfamoyl intermediates of formula 8 and 9. The present disclosure also relates to an improved process for the preparation of cobicistat using compounds of formulae 8 and 9.

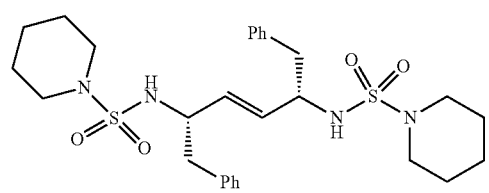

8

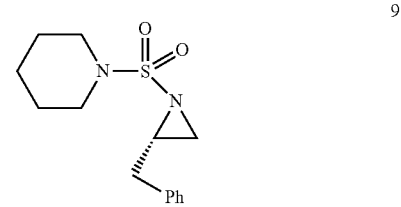

9

3 Claims, 2 Drawing Sheets

PREPARATION OF COBICISTAT INTERMEDIATES

CROSS-REFERENCE TO RELATED APPLICATIONS

This application is a national stage filing of PCT application no. PCT/IB2014/066500, filed Dec. 2, 2014, which in turn claimed priority to and the benefit of priority to IN5570/CHE/2013, filed on Dec. 3, 2013.

FIELD OF THE INVENTION

The present disclosure relates to novel crystalline piperidine sulfamoyl intermediates generated in the preparation of cobicistat by an improved synthetic process for preparation of cobicistat. The present disclosure also relates to said improved process for the preparation of cobicistat using the aforementioned novel piperidine sulfamoyl compounds.

BACKGROUND OF THE INVENTION

Cobicistat is a potent inhibitor of cytochrome P450 3A enzymes, including the important CYP3A4 subtype. It also inhibits intestinal transport proteins, and thereby may increase the overall absorption of several HIV medications, including atazanavir, darunavir, and tenofovir alafenamide fumarate.

Cobicistat is chemically known as 1,3-thiazol-5-ylmethyl [(2R,5R)-5-{[(2S)2-[(methyl {[2-(propan-2-yl)-1,3-thiazol-4-yl]methyl}carbamoyl)amino]-4-(morpholin-4yl)butanoyl]amino}-1,6-diphenylhexan-2-yl]carbamate, illustrated in Formula 1 below.

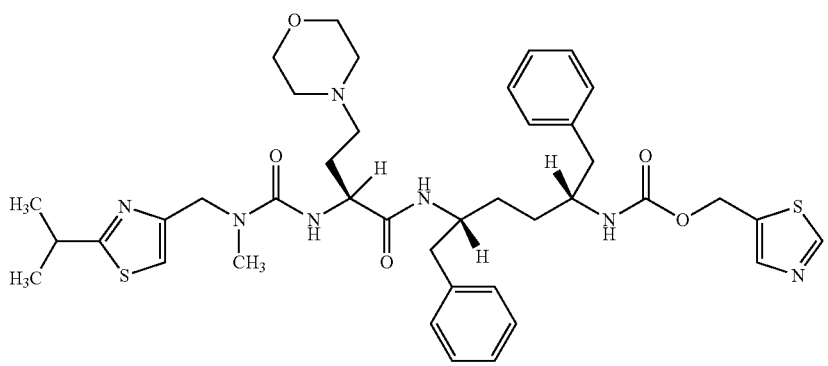

Formula 1

U.S. Pat. No. 8,148,374 patent (which is hereby incorporated by reference) discloses cobicistat and pharmaceutically acceptable salts thereof.

The present disclosure provides a novel crystalline compound of formula 8 and an improved process for the preparation of cobicistat using compound of formula 8.

SUMMARY OF THE INVENTION

A first aspect of the present disclosure is to provide the crystalline piperidine sulfamoyl compounds of formula 8 and formula 9:

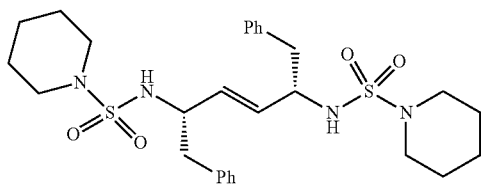

8

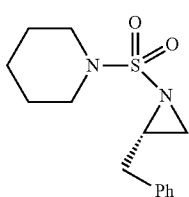

9

In one aspect, the present disclosure provides a process for the preparation of crystalline piperidine sulfamoyl dimer of formula 8, comprising the steps of a) reacting the benzyl aziridine of formula 10 with piperidine-1-sulfonylchloride in the presence of a base to create crystalline piperidine sulfamoyl aziridine of formula 9;

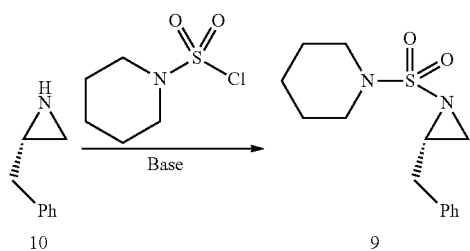

b) converting the compound of formula 9 to piperidine sulfamoyl dimer of formula 8 in presence of a base, and

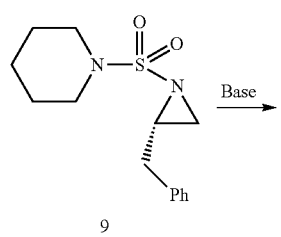

9

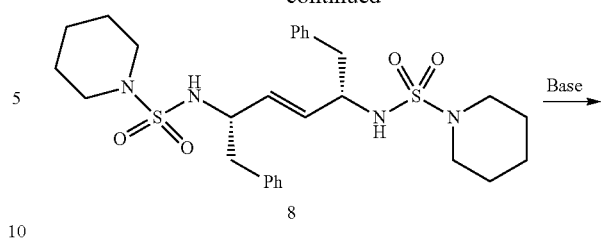

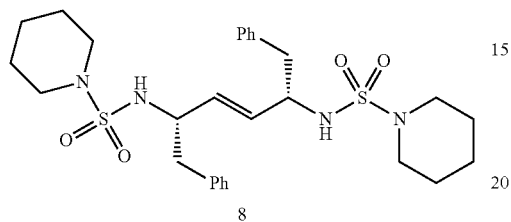

8 c) isolating the crystalline piperidine sulfamoyl dimer of formula 8.

The base in step a) above may be a weak organic or inorganic base. In some embodiments, the base may be triethylamine, diethylamine, diisopropylethylamine, pyridine, or mixtures thereof. Step a) may occur using a chlorinated organic solvent.

The process may also include the step of quenching the reaction mass that includes formula 9 with an acid after step a). In some embodiments, the process may also include a step of purifying formula 9 from the reaction mass by introducing an alcohol into the reaction mass before step b). This purifying step may result in formation of a crystalline form of formula 9. That crystalline form of formula 9 may be dissolved into a hydrocarbon solvent after its purification.

The base in step b) above may be an organic base and in some embodiments may be lithium tetramethylpiperidide (LTMP), n-butyl lithium, lithium diisopropylamide, or mixtures thereof.

In another aspect, the present disclosure provides novel crystalline compounds of formula 8, characterized by the powder X-ray diffraction pattern shown in FIG. 1 and of formula 9, characterized by the X-ray diffraction pattern shown in FIG. 2.

Yet another aspect of the present disclosure provides a process for the preparation of cobicistat as depicted in the following synthetic scheme.

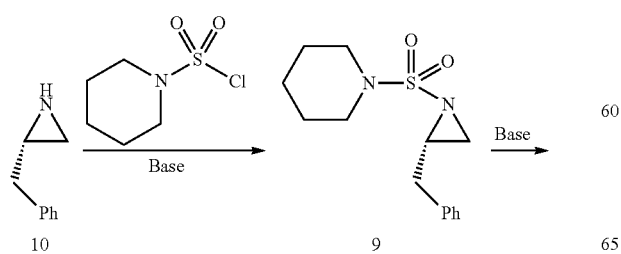

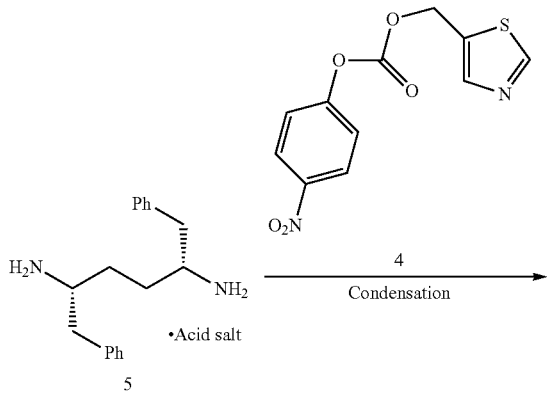

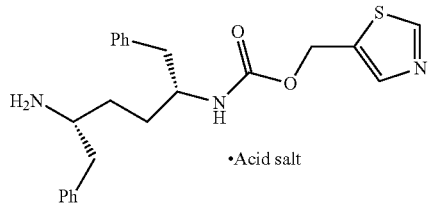

Formula 3 may then be employed in the preparation of cobicistat by condensing formula 2 with formula 3, per the prior art as discussed below.

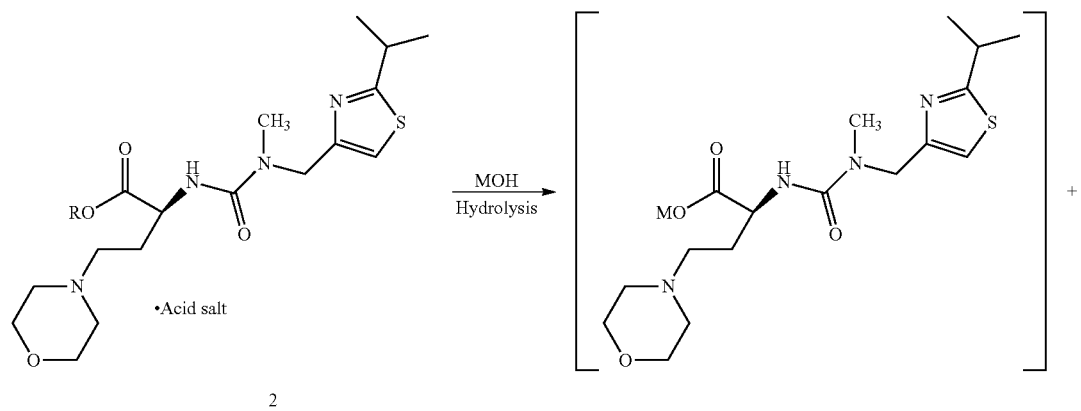

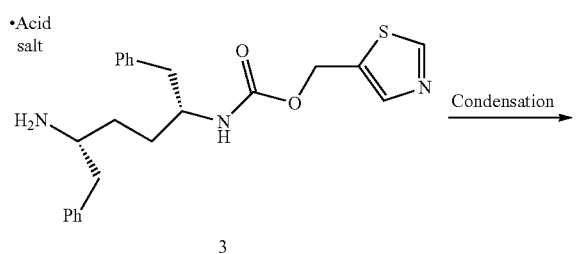

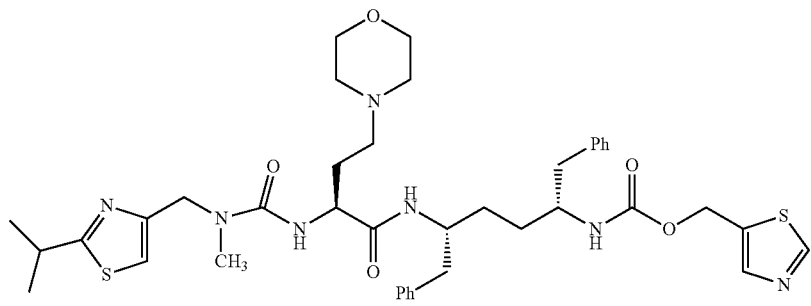

Formula 1 (Cobicistat)

R is C$_{1-4}$ alkyl
M is Na, Ca, K, Mg or Cs

BRIEF DESCRIPTION OF THE DRAWINGS

Further aspects of the present disclosure together with additional features contributing thereto and advantages accruing there from will be apparent from the following description of embodiments of the disclosure which are shown in the accompanying drawing figures wherein.

DETAILED DESCRIPTION OF THE INVENTION

Figure 1:
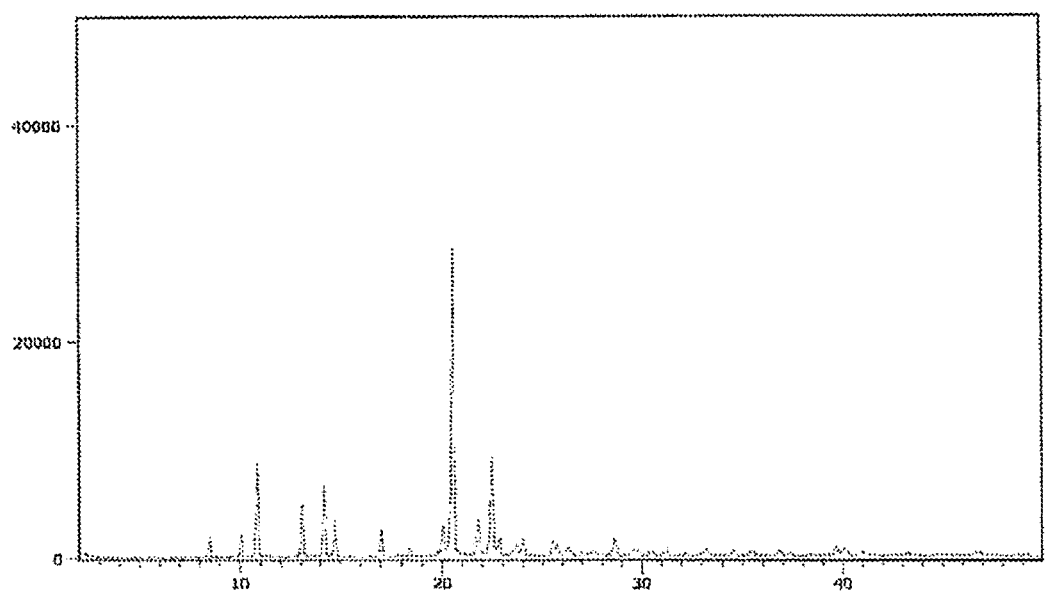
FIG. 1 is an X-ray powder diffraction pattern of crystalline compound of formula 8.

It is to be understood that the description of the present invention has been simplified to illustrate elements that are relevant for a clear understanding of the invention, while eliminating, for purposes of clarity, other elements that may be well known.

The present invention provides crystalline forms of compounds of formula 8 and formula 9. Within the context of the present invention, these crystalline intermediates possess particular utility as part of the cobicistat synthetic process.

More specifically, the present disclosure relates to a process for the preparation of piperidinyl sulfamoyl intermediates of formula 8 and 9 in crystalline form. Preparation of cobicistat utilizing these crystalline intermediates may improve yield and purity over other methods disclosed in the prior art.

In one embodiment, the present disclosure provides a process for the preparation of piperidine sulfamoyl dimer intermediate of formula 8 comprising the steps of:

a) reacting the benzyl aziridine of formula 10 with piperidine-1-sulfonylchloride in the presence of a first base to produce crystalline piperidine sulfamoyl aziridine of formula 9,

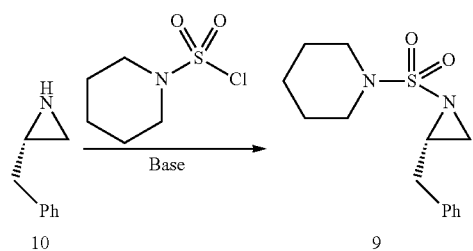

b) converting the compound of formula 9 to piperidine sulfamoyl dimer of formula 8 in presence of a second base, and

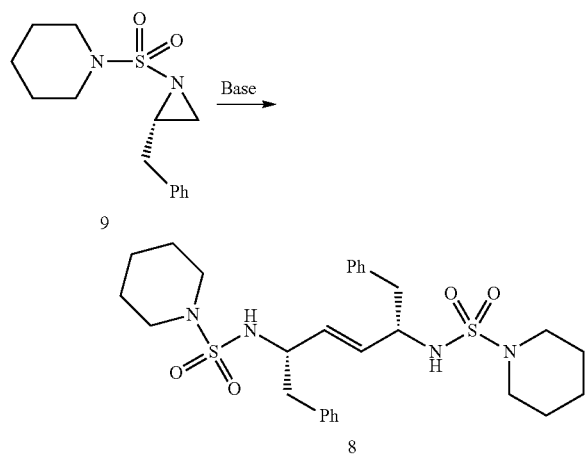

c) isolating the crystalline piperidine sulfamoyl dimer of formula 8.

According to the present disclosure, benzyl aziridine compound of formula 10 may be reacted with piperidine sulfonyl chloride in the presence of a first base in a chlorinated solvent at about −10° C. to 10° C. The reaction mass may be stirred for about 15-20 hours and neutralized with an acid. The product may then be purified in alcohol solvent to obtain crystalline piperidine sulfamoyl aziridine of formula 9.

According to the present disclosure, compound of formula 9 may then be dissolved in hydrocarbon solvent, the resulting solution is cooled to −60±10° C., and organic base is slowly added. The reaction mass may be treated with an acid to precipitate the crystalline compound of piperidine sulfamoyl dimer of formula 8.

According to the present disclosure, a chlorinated organic solvent is employed in the conversion of formula 10 to formula 9. This chlorinated organic solvent may include, for example, dichloromethane, chloroform, and mixtures thereof. One of skill in the art will recognize numerous additional chlorinated organic solvents that may be employed within the context of the present invention. In certain embodiments, it has been found that dichloromethane is a particularly useful solvent.

According to the present disclosure, a base may also be employed in the conversion of formula 10 to formula 9. In some embodiments, the base is a weak organic or inorganic base. This base may include, as examples, N,N-diisopropylethylamine, triethylamine, dimethylamine, pyridine, and mixtures thereof. One of skill in the art will recognize numerous well-known weak inorganic and organic bases that may be useful within the context of the present invention.

According to the present disclosure, an aqueous acid may be employed in the neutralization of the reaction mixture prior to isolating formula 9. The acid may be a weak or strong acid that is either organic or inorganic. In some embodiments, useful acids may include, as examples, citric acid, oxalic acid, p-toluene sulfonic acid, methanesulfonic acid, formic acid, acetic acid, fumaric acid, hydrochloric acid, sulfuric acid, and mixtures thereof. In certain embodiments, it has been found that citric acid is a particularly useful acid to quench the reaction mixture. One of skill in the art will recognize numerous well-known weak and strong inorganic and organic acids that may be useful within the context of the present invention.

According to the present disclosure, an alcohol solvent may be employed to crystallize the compound of formula 9. Examples of this solvent may include methanol, ethanol, isopropanol, butanol, and mixtures thereof. One of skill in the art will recognize numerous additional alcoholic solvents that may be employed as a solvent. In certain embodiments, it has been found that isopropyl alcohol is a particularly useful solvent.

According to the present disclosure, formula 9 may be dissolved in a hydrocarbon solvent, which may include, as examples, n-hexane, cyclohexane, methylcyclohexane, n-heptane, or mixture thereof. One of skill in the art will recognize numerous additional hydrocarbon solvents that may be employed as a solvent. In certain embodiments, it has been found that n-heptane is a particularly useful solvent.

According to the present disclosure, a second base may be employed in the conversion of formula 9 to formula 8. In some embodiments, this second base may be an organic base, and may include, as examples, lithium tetramethylpiperidide, n-butyl lithium, lithium diisopropylamide, and mixtures thereof. One of skill in the art will recognize numerous well-known organic bases that may be useful within the context of the present invention.

According to the present disclosure, the intermediate of formula 3 may be prepared from formula 8 as outlined below.

According to the present disclosure, formula 8 may then be deprotected in the presence of a base in a solvent at 100-140° C. for 10-15 hours to obtain formula 7. Within the context of the present invention, the solvent employed for deprotection of formula 8 may include, for example, toluene, xylene, benzene, and mixtures thereof. One of skill in the art will recognize numerous additional aromatic hydrocarbon solvents that may be employed within the context of the present invention. In certain embodiments, it has been found that toluene is a particularly useful solvent. Within the context of the present invention, the base may include, for example, diethylenetriamine, 1,3-diaminopropane, and mixtures thereof. In certain embodiments, it has been found that diethylenetriamine is a particularly useful base.

Formula 7 may then be reduced in the presence of a metal catalyst for 10-12 hours at room temperature under hydrogen atmosphere with a pressure of about 5 kg/m² to get formula 6. The catalyst may include, as examples, palladium on carbon, platinum oxide, rhodium, and Raney nickel. In certain embodiments, it has been found that palladium carbon is a particularly useful catalyst.

According to the present disclosure, formula 6 may then be treated with an acid to get formula 5. This acid may include, for example, hydrochloric acid, hydrobromic acid, sulfuric acid, oxalic acid, malic acid, methane sulfonic acid, or p-toluene sulfonic acid.

Formula 5 may then be condensed with formula 4 in the presence of chlorinated solvent at about 35-50° C. for 20-25 hours to get formula 3. Within the context of the present invention, the chlorinated solvent may be, as examples, dichloromethane, dichloroethane, chloroform, carbon tetrachloride, and mixture thereof.

The synthesis of formula 2, as well as the preparation of cobicistat by condensing formula 2 with formula 3, is disclosed in U.S. Pat. No. 8,497,396, which is hereby incorporated by reference.

With all of the reactions disclosed above, one of skill in the art will recognize that the reaction conditions (e.g., reaction time or temperature) may be adjusted to achieve appropriate yield without undertaking undue experimentation and without departing from the scope of the present disclosure.

The crystalline polymorph forms of compounds disclosed in the present invention may be characterized by X-ray powder diffraction ("XRPD") pattern. Thus, the X-ray diffraction patterns of the polymorphs of the disclosure were measured.

According to the present disclosure, the crystalline polymorphic form of the present disclosure is characterized by its X-ray powder diffraction pattern measured on BRUKER D-8 Discover powder diffractometer equipped with goniometer of θ/2θ configuration and Lynx Eye detector. The Cu-anode X-ray tube was operated at 40 kV and 30 mA. The experiments were conducted over the 2θ range of 2.0°-50.0°, 0.030° step size and 0.4 seconds step time.

Yet another embodiment of the present invention is the crystalline piperidine sulfamoyl dimer of formula 8:

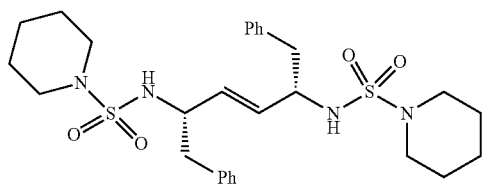

is characterized by an XRPD pattern that contains significant peaks at 2θ angles at about 10.84, 13.11, 14.20, 17.04, 20.53, 21.81 and 22.48±0.2°.

According to the present disclosure, formula 8 may be further characterized by XRPD pattern that contains significant peaks at 2θ angles at about 8.4, 10.07, 11.35, 14.75, 18.41, 19.12, 20.04, 22.85, 23.43, 23.68, 24.04, 25.53, 25.76, 26.27, 27.00, 27.34, 27.63, 27.96, 28.66, 29.62, 29.77, 30.46, 31.21, 32.25, 33.27, 34.55, 35.44, 36.84, 37.33, 38.33, 39.66, and 40.17°±0.2°. According to the present disclosure, XRPD pattern of formula 8 is shown in FIG. 1.

Figure 2:
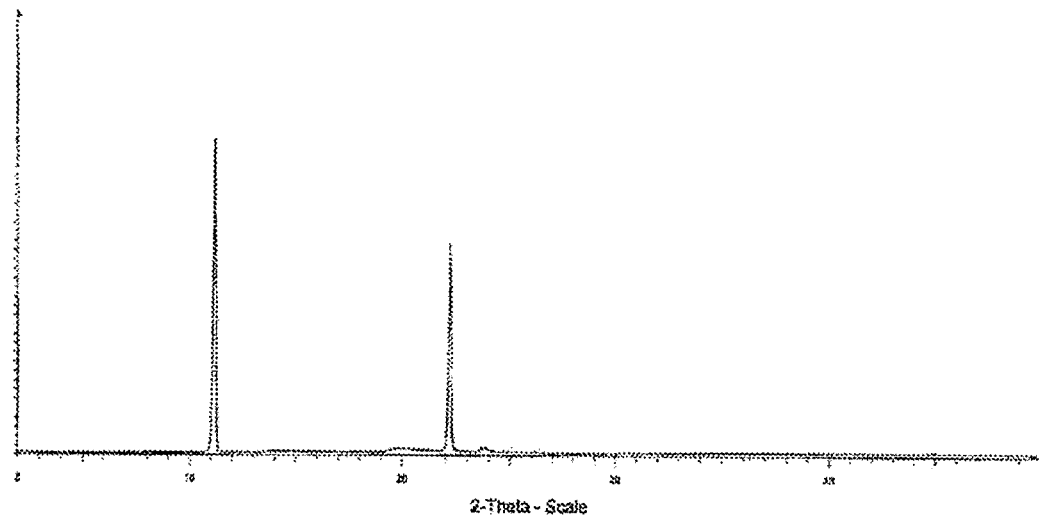
FIG. 2 is an X-ray powder diffraction pattern of crystalline compound of formula 9.

Another embodiment of the present invention is the crystalline piperidine sulfamoyl aziridine of formula 9:

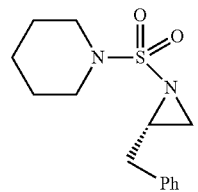

that is characterized by an XRPD pattern that contains significant peaks at 2θ angles at about 11.14 and 22.16±0.2°. According to the present disclosure, formula 9 may be further characterized by XRPD pattern that contains significant peaks at 2θ angles at about 8.05, 13.71, 19.67, 23.77, and 44.99±0.2°. According to the present disclosure, XRPD pattern of formula 8 is shown in FIG. 2.

According to the present disclosure, crystalline compounds of formula 8 and 9 are characterized by the NMR data, measured on Bruker 300 MHz Avance NMR spectrometer equipped with 5 mm BBI probe in CDCl$_3$. The data collected and processed by Topsin-NMR software.

The cobicistat and pharmaceutically acceptable salts as synthesized by the methods disclosed herein may be useful in the treatment of individuals infected with HIV, as cobicistat has been demonstrated to be an effective HIV inhibitor. Cobicistat may be used singly or in combination with other drugs, such as elvitegravir.

In some embodiments, the cobicistat of the present invention may be included in tablets for oral administration. One of skill in the art will recognize a wide variety of pharmaceutically acceptable excipients that may be included in such a tablet formulation, including lactose monohydrate, microcrystalline cellulose, croscarmellose sodium, hydroxypropyl cellulose, sodium lauryl sulfate, and magnesium stearate.

The cobicistat disclosed herein may be combined with additional active pharmaceutical components for the treatment of viral infections, including HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD inhibitors, NADH-oxidase inhibitors, CCR5 inhibitors, capsid polymerization inhibitors, other drugs for treating HIV, interferons, ribavirin, NS3 protease inhibitors, alpha-glucosidase 1 inhibitors, hepatoprotectants, non-nucleoside inhibitors of HCV, NS5a inhibitors, NS5b polymerase inhibitors, other drugs for treating HCV, and combinations thereof. In some particularly useful embodiments, the amorphous solid dispersions of cobicistat disclosed herein may be formulated in a solid dosage form that may include elvitegravir, emtricitabine, tenofovir disoproxil fumarate, atazanavir, or combinations thereof.

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many aspects and embodiments contemplated by the present disclosure.

EXAMPLE 1

Piperidine-1-sulfonyl chloride

To a solution of sulfurylchloride (238 g, 1.76 moles) in dichloromethane (500 ml), a mixture of piperidine (100 g, 1.17 moles) and triethylamine (178 g, 1.76 moles) in dichloromethane (500 ml) was added at 0° C.-5° C. The reaction mass was warmed to room temperature, stirred for 2 hours, and quenched in ice cold water. After washing with water (2×5 volumes), the organic layer was separated organic layer. The reaction mass was dried over sodium sulfate and solvent evaporated off to obtain oily residue (151.3 g, 70% yield). The $^1$H NMR spectra of the resulting solid was obtained to reveal the following spectral peaks: $^1$H NMR (300 MHz, CDCl$_3$) δ=1.58-1.62 (m, 2H), 1.69-1.83 (m, 4H), 3.31-3.42 (m, 4H)

EXAMPLE 2

Piperidine Sulfamoyl Aziridine of Formula 9

Piperidine-1-sulfonylchloride (138 g, 0.75 moles) was added to a cooled solution of 2-(S)-benzyl aziridine (100 g, 0.75 moles) in dichloromethane (300 ml), followed by N,N-diisopropylethylamine (102 g, 0.79 moles) at −5 to 5° C. The reaction mass was stirred at same temperature for 18 hours, quenched with 5% aqueous citric acid solution, and the organic layer was separated after washing with 5% aqueous sodium bicarbonate solution. The separated organic layer was evaporated off and the product was isolated in isopropyl alcohol to yield a white solid (136.5 g, 65% yield). The $^1$H NMR spectra of the resulting solid was obtained to reveal the following spectral peaks: $^1$H NMR (300 MHz, CDCl$_3$) δ=1.38-1.58 (m, 6H), 2.10-2.12 (d, 1H), 2.53-2.55 (d, 1H), 2.67-2.74 (m, 1H), 2.78-2.96 (m, 4H), 3.07-3.14 (m, 2H), 7.24-7.36 (m, 5H)

EXAMPLE 3

Piperidine Sulfamoyl Dimer of Formula 8

2, 2, 6, 6-tetramethylpiperidide (5 g, 0.035 moles) and tetrahydrofuran (160 ml) were added to a solution of piperidine sulfamoyl aziridine (100 g, 0.35 moles) in n-heptane at −55±5° C. To this solution, n-butyllithium (15% w/w in hexanes, 270 ml, and 0.43 moles) was added at a constant rate over a time period of at least 5 hours. The reaction mass was maintained for 1 hour at the same temperature followed by quenching the reaction mass with acetic acid and water to precipitate the product as an off-white solid (64 g, 64% yield). The $^1$H NMR spectra of the resulting solid was obtained to reveal the following spectral peaks: $^1$H NMR (300 MHz, CDCl$_3$) δ=1.43-1.64 (m, 12H), 2.78-84 (m, 4H), 2.86-2.96 (m, 8H), 4.02-4.15 (m, 4H), 5.59-5.61 (m, 2H) 7.13-7.33 (m, 10H)

EXAMPLE 4

Preparation of Compound of Formula 5

Diethylenetriamine (90 g) was added to a solution of formula 8 (100 g) in toluene (800 ml) and was heated to 110° C. Stirred the reaction mass at 110° C. for 12 hours. After cooling, the toluene solution was washed with aqueous sodium chloride solution (3×800 ml) dried over sodium sulfate, filtered to give a compound of formula 7 as toluene solution. To this toluene solution of compound formula 7 was added 10% palladium on carbon (4.5 g) and was purged with hydrogen gas and stirred under a hydrogen atmosphere (~5.5 kg/cm$^2$) for about 12 hours. The reaction mass was then filtered through celite bed and hydrogen chloride (85 g, 18% w/w solution in isopropyl alcohol) was added and the reaction mass was stirred for 4 hours at room temperature. The reaction mixture was then filtered and the obtained solid was further placed into a slurry in methanol (100 ml) and methyl tertiary butyl ether (600 ml). The above reaction mass was filtered and washed with methyl tertiary butyl ether (1200 ml) dried in vacuum to give compound of formula 5 as hydrochloride salt (45 g).

EXAMPLE 5

Preparation of Compound of Formula 3

Compound of formula 5 (100 g) was added to mixture of aqueous sodium hydroxide solution (25 g in 200 ml water) and dichloromethane (1300 ml), stirred for 1 hour at room temperature. The dichloromethane layer was separated and washed with water (2×500 ml) to give formula 5 as a free base. It was further diluted with dichloromethane (1500 ml). To this solution compound of formula 4 (carbonic acid-4-nitrophenyl-5-thiazolyl methyl ester (90 g) dissolved in dichloromethane) was added and stirred the reaction mass for 30 minutes at room temperature and further stirred the reaction mass at reflux for 24 hours. The dichloromethane was distilled off under reduced pressure until the remaining solution was about 400 ml. To this, THF (1200 ml) was added and distilled off the mixture of dichloromethane and tetrahydrofuran solution up to 400 ml. The above solution was further diluted with THF and was added diluted hydrochloric acid (30 g) concentrated hydrochloric acid diluted with water (15 ml) and stirred for 3 hours and filtered at room temperature to give compound 3 as hydrochloride salt.

EXAMPLE 6

Preparation of Morpholine Thiazole Ethyl Ester Oxalate (Salt Formula 2)

A stirred mixture of (R)-(+)-α-amino-γ-butyrolactone hydrobromide (92 g) and dichloromethane (500 ml) was cooled to −5 to −8° C. Carbonyl diimidazole (92 g) was then added to this mixture lot-wise. Triethylamine (45 g) was then added drop-wise with continued stirring until the starting material disappeared. 2-Isopropyl-4-[(N-methylamino) methyl] thiazole di-hydrochloride (100 g) and triethylamine (92 g) were then slowly added to the mixture. The reaction mixture was stirred at about at 20-25° C. for 15 hours. Water (200 ml) was added, and the organic layer was separated. The organic layer was washed with water (200 ml). The combined aqueous layers were back extracted with dichloromethane (100 ml). The collected the organic layers were then washed with 20% aqueous citric acid solution (40 g). The combined organic layer was then washed with water (200 ml). The organic layer was concentrated under reduced pressure at about 38-40° C. to obtain the crude urea N-methyl-N-[[2-(1-methylethyl)-4-thiazolyl]methyl]-N'-[(3S)-tetrahydro-2-oxo-3-furanyl] (80 g).

The solution of urea N-methyl-N-[[2-(1-methylethyl)-4-thiazolyl]methyl]-N'-[(3S)-tetrahydro-2-oxo-3-furanyl] (100 g) dichloromethane (500 ml) was stirred at room temperature and ethanol (100 ml) was added. The reaction mass was cooled to 0-5° C. and trimethylsilyl bromide (183 g) was slowly added drop-wise. The reaction mass temperature was then raised to 19-25° C. and stirred until reaction was complete. The reaction mass was cooled to 0-5° C. and morpholine was added (230 g) drop wise slowly. The temperature was then raised to 19-25° C. and the reaction mass was stirred over a period of 17 hours. The reaction mixture was then filtered to remove morpholine hydrobromide salt. The filter cake was rinsed with dichloromethane. The filtrates were washed with water and the combined organic layer was concentrated under vacuum to dryness to give a residue. The residue was dissolved in acetone (500 ml). Oxalic acid dihydrate (60 g) in acetone (400 ml) was slowly added. The resulting slurry was refluxed for about one hour and cooled to 0-5° C. The product was filtered and rinsed with acetone (200 ml) and dried under vacuum at 40° C. to produce morpholine thiazole ethyl ester oxalate formula 2 as a white to off-white solid (122 g).

EXAMPLE 7

Preparation of Cobicistat Silicon Dioxide

Thiazole ethyl ester salt (formula 2) (150 g) in water (250 ml) was added to dichloromethane (800 ml), followed by a slow addition of aqueous potassium bicarbonate (220 g of potassium bicarbonate dissolved 1.250 l of water). The resulting mixture was stirred for about 1 hour and the aqueous and organic layers were separated. The organic layer was washed with water and then concentrated under vacuum until the reaction mass volume reached about 350 ml. The reaction mass was cooled to about 5° C. An aqueous potassium hydroxide solution (about 23 g of KOH dissolved in 25 ml of water) was slowly added to the cooled reaction mass while maintaining a temperature not more than about 10° C. The mixture was then stirred for about 12 hours at the same temperature. Cobicistat intermediate of formula 3 (100 g) and dichloromethane (350 ml), were added to the mixture and the temperature was adjusted to about −20° C. Hydroxybenzotriazole hydrate (about 25 g) was then added to this mixture. A pre-cooled solution (about −20° C. of N-(3-dimethylaminopropyl)-N'-ethylcarbodiimide hydrochloride (80 g) in dichloromethane (about 800 ml)) was added to the reaction mixture while the reaction mass temperature was maintained at not more than about −20° C. The reaction mixture was then stirred at about the same temperature for 24 hours. The reaction mass temperature was then adjusted to about 5° C. and the reaction was quenched with an aqueous citric acid solution. The aqueous and organic layers were separated and the organic layer was washed once with aqueous potassium bicarbonate solution and water. The organic layer was concentrated under reduced pressure to give cobicistat (about 160 g) as a residue. The residue was dissolved in mixture of dichloromethane (160 ml) and n-hexane (160 ml) at room temperature. Silicon dioxide (150 g) was added to the mixture and stirred for 2-3 hours. The solution was concentrated, cooled, and filtered to give a cobicistat silicon dioxide product (300 g).

We claim:

1. A crystalline piperidine sulfamoyl dimer of formula 8

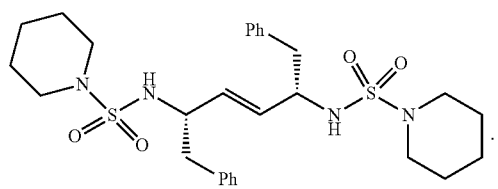

8

2. The compound of claim 1, which has an X-ray powder diffraction pattern having significant peaks at about 2θ values of 10.84, 13.11, 14.20, 17.04, 20.53 and 21.81 ±0.02°.

3. The compound of claim 1, which has an X-ray powder diffraction pattern as shown in FIG. 1.

* * * * *